(12) United States Patent
Nemec et al.

(10) Patent No.: US 10,952,629 B2
(45) Date of Patent: Mar. 23, 2021

(54) ATRAUMATIC COUPLING AND CATHETER EMPLOYING THE SAME

(71) Applicant: St. Jude Medical, Cardiology Division, Inc., St. Paul, MN (US)

(72) Inventors: Linda Kay Nemec, Andover, MN (US); Neil David Hawkinson, Ramsey, MN (US); Ryan Dale Hendrickson, Albertville, MN (US); Matthew Lee Knochenmus, Corcoran, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 16/874,305

(22) Filed: May 14, 2020

(65) Prior Publication Data

US 2020/0268268 A1 Aug. 27, 2020

Related U.S. Application Data

(62) Division of application No. 15/347,159, filed on Nov. 9, 2016, now Pat. No. 10,779,741.

(Continued)

(51) Int. Cl.
*A61B 5/04* (2006.01)
*A61B 18/18* (2006.01)
(Continued)

(52) U.S. Cl.
CPC .......... *A61B 5/0402* (2013.01); *A61B 5/6852* (2013.01); *A61B 18/1492* (2013.01);
(Continued)

(58) Field of Classification Search
CPC ...... A61B 2018/00577; A61B 18/1492; A61B 2218/002; A61B 8/12; A61B 5/0084;
(Continued)

(56) References Cited

U.S. PATENT DOCUMENTS

| 4,145,075 A | 3/1979 | Holzmann |
| 4,205,675 A | 6/1980 | Vaillancourt |

(Continued)

FOREIGN PATENT DOCUMENTS

| CH | 700731 | 10/2010 |
| GB | 2515126 | 12/2014 |

(Continued)

*Primary Examiner* — Joseph A Stoklosa
*Assistant Examiner* — Brian M Antiskay
(74) *Attorney, Agent, or Firm* — Wiley Rein LLP

(57) ABSTRACT

A catheter includes a proximal shaft and a distal shaft having differing diameters; often, the distal shaft will have a smaller diameter than the proximal shaft. A coupling joins the distal shaft to the proximal shaft. For example, a proximal portion of the distal shaft can be inserted into the coupling through its distal end, while the proximal portion of the coupling can be inserted into the proximal shaft through its distal end. To provide an atraumatic transition from the distal shaft to the proximal shaft, coupling can taper towards its distal end, for example by using a dome- or frustoconical-shape for the distal portion of the coupling. The exterior of the coupling can be ribbed to facilitate bonding to the proximal shaft. The distal shaft can be formed into at least a partial loop having a fixed or variable radius of curvature.

6 Claims, 5 Drawing Sheets

Related U.S. Application Data

(60) Provisional application No. 62/280,159, filed on Jan. 19, 2016.

(51) Int. Cl.
| | |
|---|---|
| *A61B 5/0402* | (2006.01) |
| *A61B 18/14* | (2006.01) |
| *A61M 39/12* | (2006.01) |
| *A61M 25/00* | (2006.01) |
| *A61M 25/09* | (2006.01) |
| *A61B 5/00* | (2006.01) |
| *A61M 39/10* | (2006.01) |

(52) U.S. Cl.
CPC .... *A61M 25/0014* (2013.01); *A61M 25/0023* (2013.01); *A61M 25/0069* (2013.01); *A61M 25/0905* (2013.01); *A61M 39/10* (2013.01); *A61M 39/12* (2013.01); *A61B 2018/1435* (2013.01); *A61M 2039/1027* (2013.01)

(58) Field of Classification Search
CPC .. A61B 2018/00863; A61B 2018/0212; A61B 2217/007; A61B 2018/00011; A61M 1/008; A61M 2205/3303
See application file for complete search history.

(56) References Cited

U.S. PATENT DOCUMENTS

| | | | |
|---|---|---|---|
| 6,055,868 | A | 5/2000 | Koyano et al. |
| 7,131,671 | B2 | 11/2006 | Saarem et al. |
| 7,606,609 | B2 | 10/2009 | Muranushi et al. |
| 8,714,030 | B1 | 5/2014 | Liu et al. |
| 8,728,065 | B2 | 5/2014 | Fish et al. |
| 2006/0170211 | A1 | 8/2006 | Matsubara |
| 2015/0223713 | A1 | 8/2015 | Ollivier |
| 2017/0202468 | A1 | 7/2017 | Nemec et al. |

FOREIGN PATENT DOCUMENTS

| | | |
|---|---|---|
| JP | 2007-204280 | 8/2007 |
| JP | 2011-224364 | 11/2011 |
| JP | 2011-528420 | 11/2011 |
| WO | 2004/045697 | 6/2004 |
| WO | 2007/002179 | 1/2007 |
| WO | 2009135887 | 11/2009 |

ATRAUMATIC COUPLING AND CATHETER EMPLOYING THE SAME

CROSS-REFERENCE TO RELATED APPLICATIONS

This application is a divisional of U.S. application Ser. No. 15/347,159, filed 9 Nov. 2016 ("the '159 application"), which claims the benefit of U.S. provisional application No. 62/280,159, filed 19 Jan. 2016 ("the '159 provisional"). The '159 application and the '159 provisional are hereby incorporated by reference as though fully set forth herein.

BACKGROUND

The instant disclosure relates to catheters for use in medical procedures, such as electrophysiology studies. In particular, the instant disclosure relates to an atraumatic coupling that can be used to join two shafts of unequal size.

Catheters are used for an ever-growing number of procedures, such as diagnostic, therapeutic, and ablative procedures, to name just a few examples. Typically, the catheter is manipulated through the patient's vasculature and to the intended site, for example, a site within the patient's heart.

A typical electrophysiology catheter includes an elongate shaft and one or more electrodes on the distal end of the shaft. The electrodes may be used for ablation, diagnosis, or the like. Oftentimes, these electrodes are ring electrodes that extend about the entire circumference of the catheter shaft.

One specific use of an electrophysiology catheter is to map the atrial regions of the heart, and in particular the pulmonary veins, which are often origination points or foci of atrial fibrillation. Such electrophysiology mapping catheters typically have at least a partial loop shape at their distal end, oriented in a plane generally orthogonal to the longitudinal axis of the catheter shaft, which allows the loop to surround the pulmonary vein ostia.

Further, the more proximal and elongate region of the shaft often has a larger diameter than the more distal region (e.g., the portion formed into at least a partial loop). Thus, there is a need to transition from the larger diameter proximal shaft to the smaller diameter distal shaft.

BRIEF SUMMARY

Disclosed herein is a catheter including: a proximal shaft having a first diameter; a distal shaft having a second diameter different from the first diameter; and a coupling joining the proximal shaft to the distal shaft, the coupling having a hollow interior and including a distal portion and a proximal portion, wherein a proximal portion of the distal shaft is inserted into the hollow interior of the coupling through a distal end of the coupling and the proximal portion of the coupling is inserted into the proximal shaft through a distal end of the proximal shaft.

In embodiments, the catheter also includes a sensor having a hollow core disposed within a distal portion of the proximal shaft, wherein the proximal portion of the coupling is inserted into the hollow core of the sensor and the distal portion of the proximal shaft. The proximal portion of the coupling can include a first sub-portion having an outer diameter small enough to allow insertion into the hollow core of the sensor; and a second sub-portion having an outer diameter small enough for insertion into the distal portion of the proximal shaft, but too large for insertion into the hollow core of the sensor, wherein the second sub-portion is positioned distally of the first sub-portion.

According to aspects of the disclosure, an outer diameter of the coupling is smaller at the distal end of the coupling than at a point adjacent the distal end of the proximal shaft. For example, the distal portion of the coupling comprises can include dome shaped portion and/or a frustoconical portion.

According to other aspects of the disclosure, a maximum outer diameter of the proximal portion of the coupling is less than a maximum outer diameter of the distal portion of the coupling.

The hollow interior of the coupling can include an abutment surface for the proximal portion of the distal shaft, which stops the advancement of the distal shaft into the coupling at a desired depth. It is also contemplated that the coupling can cause the distal shaft to be positioned coaxially within the proximal shaft.

In embodiments, an exterior surface of the coupling includes a plurality of ribs. The coupling can also be made out of a clear polymeric material, for example to facilitate visualization of the distal shaft within the coupling.

The distal shaft can be formed into at least a partial loop. The radius of curvature of the loop can be fixed or variable.

Also disclosed herein is a method of manufacturing a catheter, including: providing a proximal shaft having a first diameter, a distal shaft having a second diameter different from the first diameter, and a coupling having a hollow interior; inserting a proximal portion of the distal shaft into the hollow interior of the coupling through a distal end of the coupling; inserting a proximal portion of the coupling into the proximal shaft through a distal end of the proximal shaft; securing the distal shaft to the coupling; and securing the proximal shaft to the coupling.

The hollow interior of the coupling can include an inner abutment surface, such that inserting a proximal portion of the distal shaft into the hollow interior of the coupling through a distal end of the coupling can include advancing the proximal portion of the distal shaft into the hollow interior of the coupling until a proximal end of the distal shaft abuts the inner abutment surface. Similarly, an exterior surface of the coupling can include an outer abutment surface, such that inserting a proximal portion of the coupling into the proximal shaft through a distal end of the proximal shaft can include advancing the proximal portion of the coupling into the proximal shaft until the distal end of the proximal shaft abuts the outer abutment surface.

According to aspects of the disclosure, the manufacturing method also includes: providing a sensor having a hollow core; inserting the proximal portion of the coupling into the hollow core of the sensor; and inserting the proximal portion of the coupling and the sensor into the proximal shaft through the distal end of the proximal shaft.

The distal shaft, coupling, and proximal shaft can be secured to each other, for example, using an ultraviolet curing adhesive.

In another aspect, the present disclosure provides an atraumatic coupling for securing a first shaft segment to a second shaft segment having a different outer diameter from the first shaft segment. The coupling includes: a proximal portion having an exterior surface, the exterior surface of the proximal portion including a plurality of ribs, and wherein an outer diameter of the proximal portion is not greater than an inner diameter of the first shaft segment; and a distal portion, the distal portion having an exterior surface that tapers from a point at which the proximal portion meets the distal portion to a distal tip of the distal portion, and wherein an outer diameter of the distal portion at the point at which the proximal portion meets the distal portion is about equal to an outer diameter of the first shaft segment, wherein at least the distal portion defines an interior cavity of the coupling, and wherein a diameter of the interior cavity of the coupling is not smaller than an outer diameter of the second shaft segment. It is contemplated that the coupling can include a clear polymeric material.

The foregoing and other aspects, features, details, utilities, and advantages of the present invention will be apparent from reading the following description and claims, and from reviewing the accompanying drawings.

DETAILED DESCRIPTION

For the sake of illustration, certain embodiments of the disclosure will be explained herein with reference to an electrophysiology catheter utilized in cardiac electrophysiology studies. It should be understood, however, that the present teachings may be applied to good advantage in other contexts as well.

Figure 1:
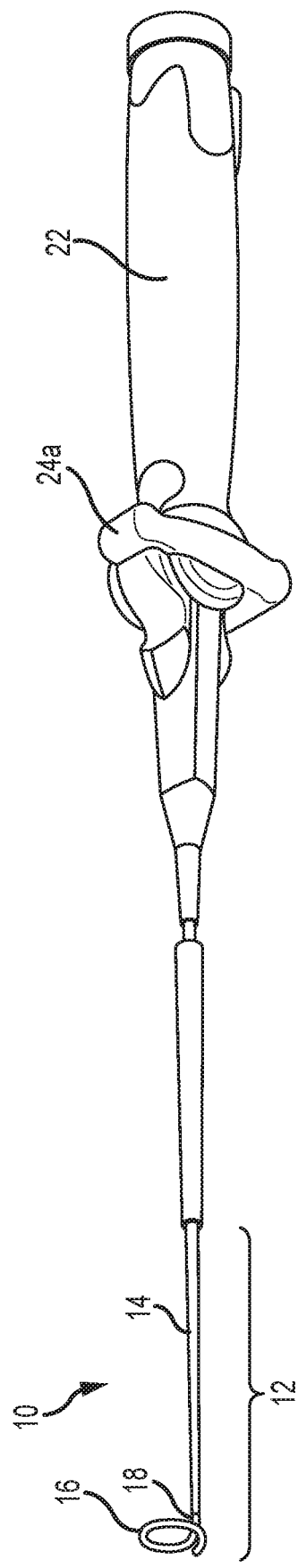
FIGS. 1 and 2 illustrate exemplary electrophysiology catheters.
Figure 2:
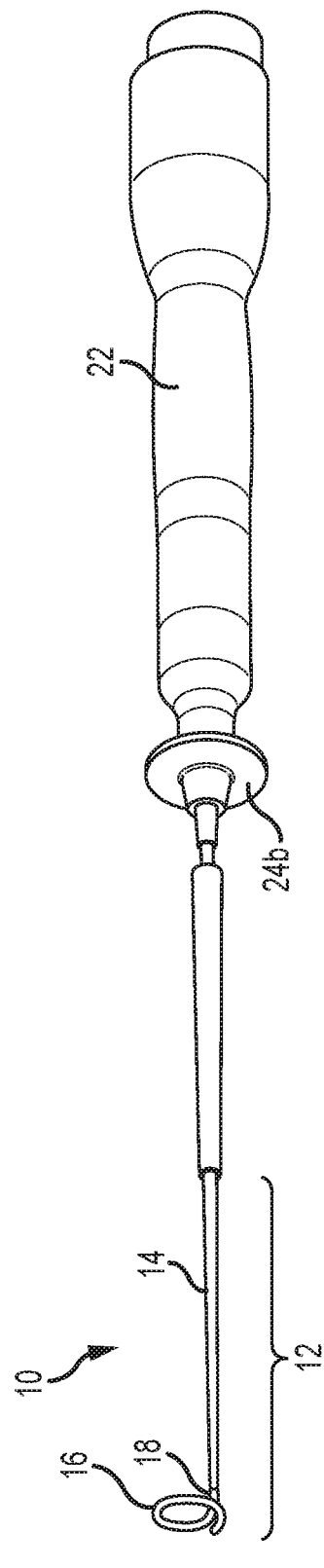

Referring now to the figures, FIGS. 1 and 2 depict two embodiments of an electrophysiology ("EP") catheter 10 according to aspects of the present disclosure. EP catheter 10 includes catheter body 12, which in turn includes a proximal shaft 14, a distal shaft 16, and a coupling 18 that joins proximal shaft 14 and distal shaft 16 as discussed herein. In some embodiments, catheter body 12 is tubular (e.g., it defines at least one lumen therethrough). It should also be understood that the relative lengths of proximal shaft 14, distal shaft 16, and coupling 18 as depicted in FIGS. 1 and 2 are merely illustrative and may vary without departing from the spirit and scope of the instant disclosure. Of course, the overall length of catheter body 12 should be long enough to reach the intended destination within the patient's body.

Catheter body 12 will typically be made of a biocompatible polymeric material, such as polytetrafluoroethylene (PTFE) tubing (e.g., TEFLON® brand tubing). Of course, other polymeric materials, such as fluorinated ethylene-propylene copolymer (FEP), perfluoroalkoxyethylene (PFA), poly(vinylidene fluoride), poly(ethylene-co-tetrafluoroethylene), and other fluoropolymers, may be utilized. Additional suitable materials for catheter body 12 include, without limitation, polyamide-based thermoplastic elastomers (namely poly(ether-block-amide), such as PEBAX®), polyester-based thermoplastic elastomers (e.g., HYTREL®), thermoplastic polyurethanes (e.g., PEL-LETHANE®, ESTANE®), ionic thermoplastic elastomers, functionalized thermoplastic olefins, and any combinations thereof. In general, suitable materials for catheter body 12 may also be selected from various thermoplastics, including, without limitation, polyamides, polyurethanes, polyesters, functionalized polyolefins, polycarbonate, polysulfones, polyimides, polyketones, liquid crystal polymers and any combination thereof. It is also contemplated that the durometer of catheter body 12 may vary along its length. In general, the basic construction of catheter body 12 will be familiar to those of ordinary skill in the art, and thus will not be discussed in further detail herein except to the extent necessary to understand the instant disclosure.

Figure 3:
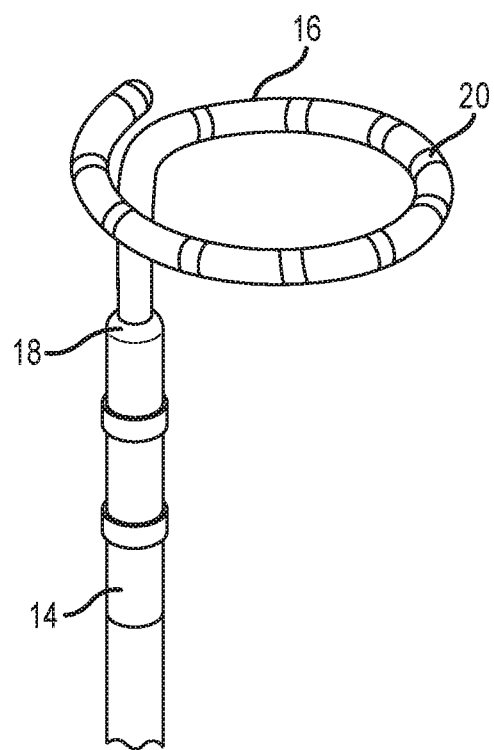
FIG. 3 is a close up of a portion of an electrophysiology catheter according to some embodiments of the instant disclosure.

As seen in FIG. 3, distal shaft 16 can be predisposed into at least a partial loop. This loop shape allows distal shaft 16 to conform to the shape, for example, of a pulmonary vein ostium. The partial loop may take a number of configurations, depending on the intended or desired use of EP catheter 10, consistent with the present teachings. Therefore, it should be understood that the loop configuration depicted in FIG. 3 is merely illustrative.

FIG. 3 also illustrates that distal region 16 can include a plurality of electrodes 20 disposed thereon. Electrodes 20 may be ring electrodes or any other electrodes suitable for a particular application of EP catheter 10. For example, where EP catheter 10 is intended for use in a contactless electrophysiology study, electrodes 20 may be configured as described in U.S. application Ser. No. 12/496,855, filed 2 Jul. 2009, which is hereby incorporated by reference as though fully set forth herein. Of course, in addition to serving sensing purposes (e.g., cardiac mapping and/or diagnosis), electrodes 20 may be employed for therapeutic purposes (e.g., cardiac ablation and/or pacing).

FIG. 3 further illustrates that the outer diameter of proximal shaft 14 differs from the outer diameter of distal shaft 16. For example, the outer diameter of proximal shaft 14 can be 8 French (0.104 inches), while the outer diameter of distal shaft 16 can be 4 French (0.052 inches). Thus, coupling 18 secures proximal shaft 14 to distal shaft 16 while providing an atraumatic transition from the outer diameter of one to the outer diameter of the other as discussed in further detail below. This is also illustrated to good advantage in FIG. 4.

Referring again to FIGS. 1 and 2, a handle 22 is coupled to catheter body 12. Handle 22 includes suitable actuators (e.g., actuator 24a in FIG. 1; actuator 24b in FIG. 2) to control the deflection of catheter body 12, for example as described in U.S. Pat. No. 8,369,923, which is hereby incorporated by reference as though fully set forth herein. Various handles and their associated actuators for use in connection with electrophysiology catheters are known, and thus handle 22 will not be described in further detail herein.

Although in some embodiments, the radius of curvature of the loop of distal shaft 16 may be fixed, it is also contemplated that it may be adjustable, for example to conform to the varying sizes of pulmonary vein ostia of patients of different ages. This additional control may be provided, for example, via the use of an activation wire that is adapted to alter the radius of curvature of the loop of distal shaft 16. One suitable material for such an activation wire is stainless steel, though other materials can be employed without departing from the spirit and scope of the instant disclosure.

In some embodiments, one end (e.g., the distal end) of the activation wire may be coupled to the tip of catheter body 12 (e.g., coupled to a distal-most tip electrode of electrodes 20), while the other end (e.g., the proximal end) of the activation wire may be coupled to an actuator (e.g., a thumb slider) on handle 22. Thus, for example, sliding the thumb slider proximally can place the activation wire in tension, thereby altering the radius of curvature of the loop of distal shaft 16.

Another exemplary mechanism for varying the radius of curvature of the loop of distal shaft 16 is described in U.S. Pat. No. 7,606,609, which is hereby incorporated by reference as though fully set forth herein.

Figure 5A:
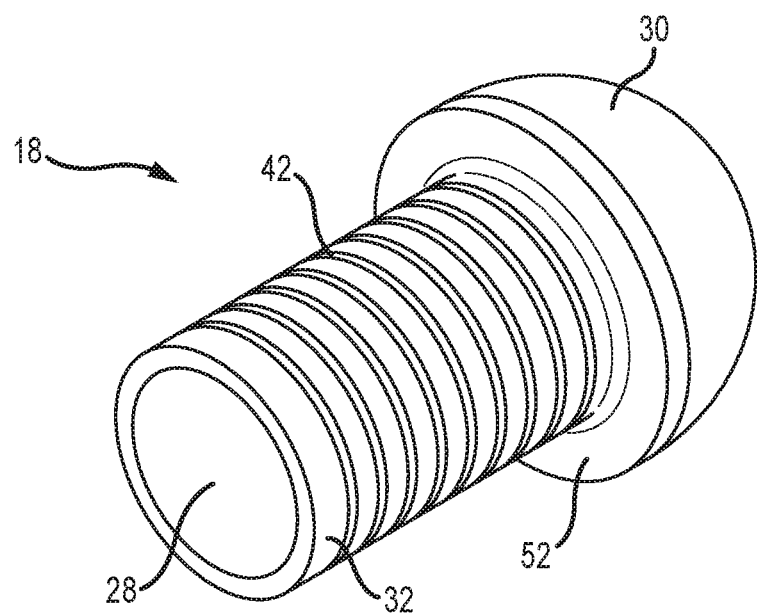
FIG. 5A is a perspective view of an embodiment of a coupling as disclosed herein.
Figure 5B:
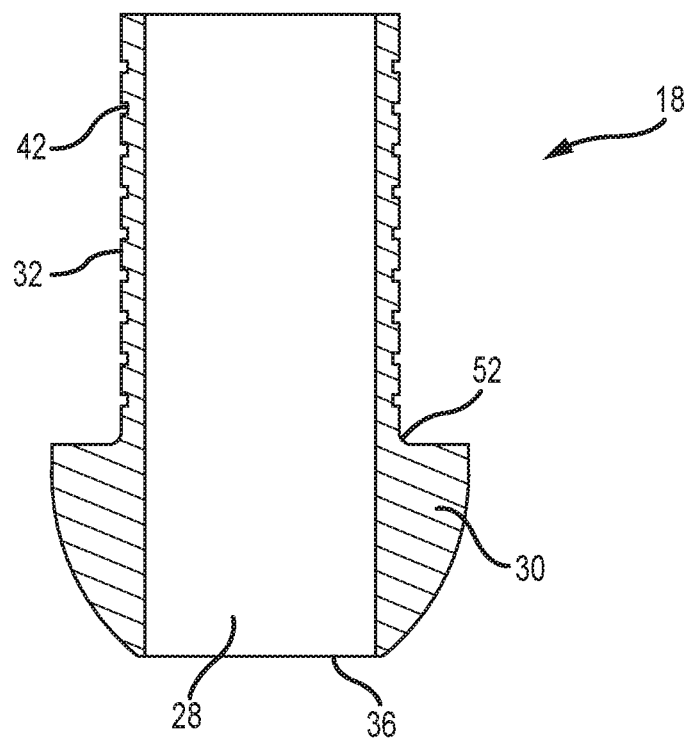
FIG. 5B is a cross-sectional view of the coupling of FIG. 5A.

A first embodiment of coupling 18 is depicted in perspective view in FIG. 5A and in cross-section in FIG. 5B. As shown in FIGS. 5A and 5B, coupling 18 includes a hollow interior 28. As used herein, the term "hollow interior" means that there is at least one cavity within the interior; the term "hollow core" is used synonymously in this disclosure. Although this cavity is depicted in FIGS. 5A and 5B as extending throughout the entire length of coupling 18 with a substantially constant diameter, the term "hollow" is not intended to be so limited. Thus, the diameter of the cavity can vary along the length of coupling 18 and still be considered "hollow" within the meaning of the instant disclosure.

Coupling 18 includes a distal portion 30 and a proximal portion 32. As shown in the simplified assembly drawing of FIG. 6, distal portion 30 of coupling 18 receives distal shaft 16 (e.g., the proximal portion 34 of distal shaft 16 is inserted into hollow interior 28 of coupling 18 through the distal end 36 of coupling 18). Similarly, proximal portion 32 of coupling 18 is received into proximal shaft 14 (e.g., proximal portion 32 of coupling 18 is inserted into proximal shaft 14 through the distal end 38 of proximal shaft 14).

Figure 6:
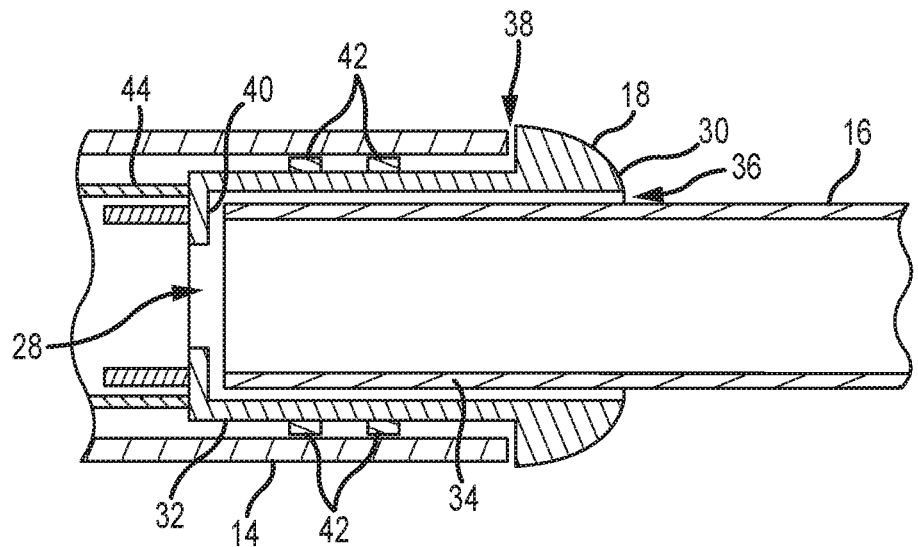
FIG. 6 is a simplified cross-sectional assembly drawing of a distal shaft, a proximal shaft, a coupling, and a sensor as disclosed herein.

FIGS. 5A, 5B, and 6 also illustrate that the outer diameter of coupling 18 changes along its length. In particular, the outer diameter of coupling 18 is narrower at its distal end 36 than it is at a point adjacent distal end 38 of proximal shaft 14. That is, distal portion 30 of coupling 18 tapers towards its distal end 36 and can, in embodiments, include a dome-shape as shown in FIGS. 5A, 5B, and 6. In other embodiments, such as shown in FIG. 7, distal portion 30 of coupling 18 can include a frustoconical shape.

Figure 4:
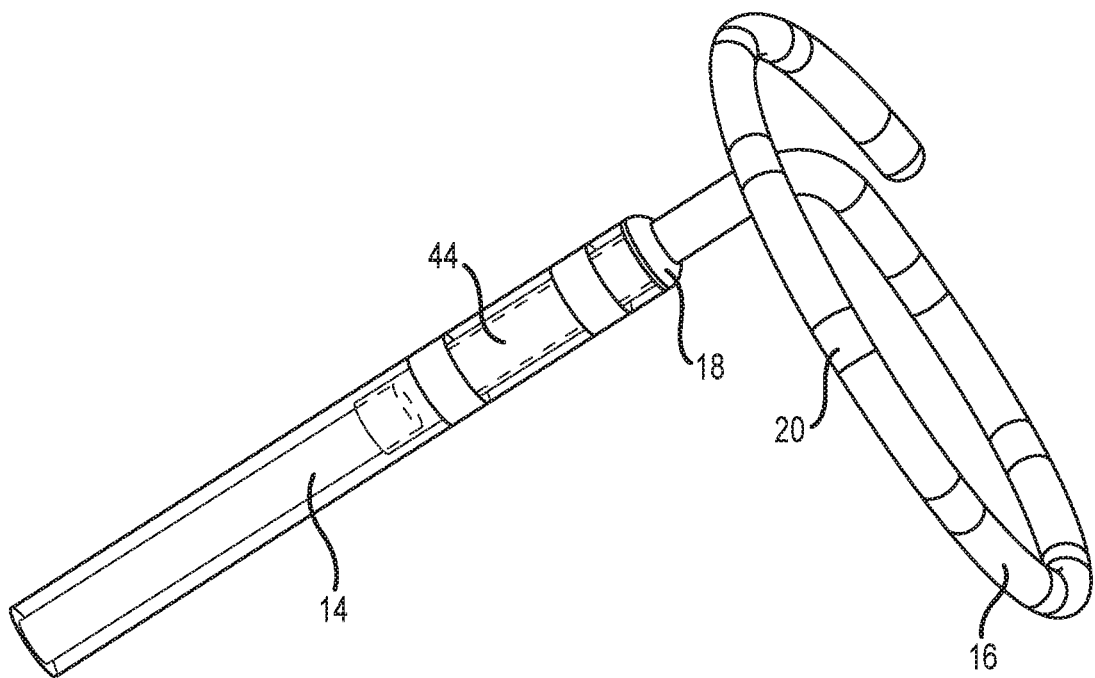
FIG. 4 depicts the assembly of a distal shaft, a proximal shaft, a coupling, and a sensor according to aspects of the disclosure.

According to aspects of the disclosure, the maximum outer diameter of proximal portion 32 of coupling 18 is less than the maximum outer diameter of distal portion 30 of coupling 18. It is further contemplated that the outer diameter of the distal portion 30 of coupling 18 where distal portion 30 meets proximal portion 32 (e.g., a point adjacent distal end 38 of proximal shaft 14 when catheter 10 is assembled) is about equal to the outer diameter of proximal shaft 14 in order to facilitate a smooth transition to proximal shaft 14. Thus, for example, if proximal shaft 14 has an 8 French outer diameter, then the outer diameter of coupling 18 where distal portion 30 thereof transitions to proximal portion thereof can also be about 8 French. There can, however, be about an 8% difference in these outer diameters without adversely affecting the smooth and atraumatic transition provided by the combination of the tapering shape of distal portion 30 and the relative diameters of distal portion 30, proximal portion 32, and proximal shaft 14 (e.g., as shown in FIG. 4).

Figure 7:
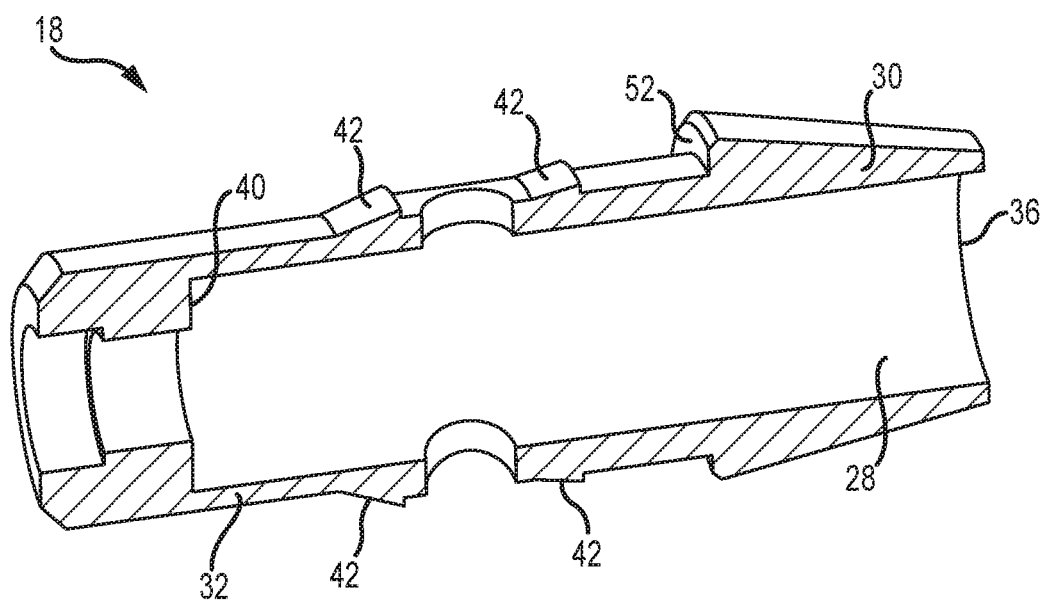
FIG. 7 is a cross-sectional view of another embodiment of a coupling as disclosed herein.

As shown in FIGS. 6 and 7, proximal portion 32 of coupling 18 can include an abutment surface 40. Abutment surface 40 stops the advancement of distal shaft 16 into hollow interior 28 of coupling 18. That is, distal shaft 16 is advanced into hollow interior 28 of coupling 18 until the proximal portion 34 of distal shaft 16 abuts the abutment surface 40 (see FIG. 6).

The exterior surface of proximal portion 32 of coupling 18 can also include one or more ribs 42. Ribs 42 can increase the bondability between coupling 18 and proximal shaft 14, for example by creating a mechanical lock with the adhesive used to attach coupling 18 to proximal shaft 14.

Figure 8:
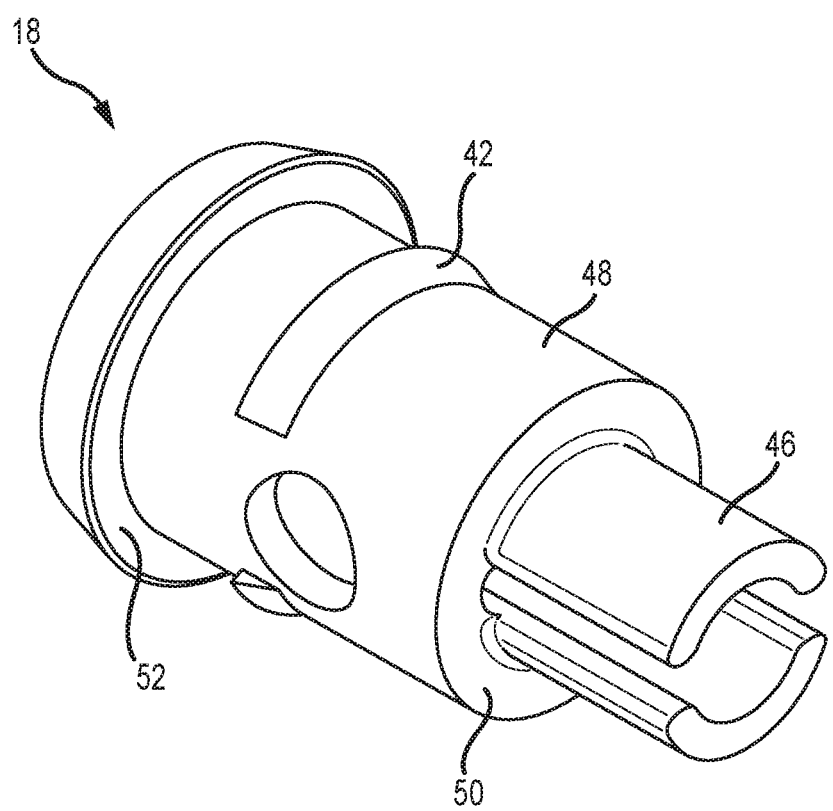
FIG. 8 is a perspective view of still another embodiment of a coupling as disclosed herein.

FIG. 8 depicts an additional embodiment of coupling 18 that is configured to facilitate the positioning of an additional sensor 44 (shown in FIGS. 4 and 6) along catheter body 12. In the embodiment of coupling 18 depicted in FIG. 8, proximal portion 32 of coupling 18 includes a first sub-portion 46 and a second sub-portion 48. First sub-portion 46 has an outer diameter small enough for insertion into a hollow core of sensor 44 such that, for example, sensor 44 is advanced until it abuts surface 50 at the transition between first and second sub-portions 46, 48 (which can be the opposite side of abutment surface 40 against which distal shaft 16 abuts).

Second sub-portion 48, which is distal of first sub-portion 46, has an outer diameter small enough for insertion into proximal shaft 14, but too large for insertion into the hollow core of sensor 44. Second sub-portion 48 (and thus proximal portion 32) ends at surface 52, which restricts the advancement of coupling 18 into proximal shaft 14 during assembly.

Alternatively, coupling 18 can also serve as a datum for positioning one or more sensors 44 without having coupling 18 inserted therein.

In embodiments, coupling 18 can be made of a clear polymeric material. The use of a clear polymeric material enables the use of an ultraviolet curing adhesive to join coupling 18 to distal shaft 16. It also facilitates visual confirmation that distal shaft 16 is properly positioned within coupling 18. Of course, in other embodiments, coupling 18 can be translucent or opaque.

Assembly of catheter body 12 can be understood with reference to FIG. 6. Distal shaft 16 is inserted into hollow interior 28 of coupling 18 through the distal end 36 of coupling 18 until proximal portion 34 of distal shaft 16 reaches the abutment surface 40 within proximal portion 32 of coupling 18.

Optionally, a hollow core sensor 44 can be fit over first sub-portion 46 of proximal portion 32 of coupling 18, for example until sensor 44 abuts surface 50. Proximal portion 32 of coupling 18 (and sensor 44, if present) can then be inserted into proximal shaft 14 through distal end 38 of proximal shaft 14, for example until distal end 38 of proximal shaft 14 abuts surface 52.

Advantageously, coupling 18 facilitates coaxial alignment between proximal shaft 14, sensor 44 (if present), and distal shaft 16. Once the desired alignment is achieved, the various components can be secured to one another, for example via the use of an ultraviolet curing adhesive.

Although several embodiments of this invention have been described above with a certain degree of particularity, those skilled in the art could make numerous alterations to the disclosed embodiments without departing from the spirit or scope of this invention.

For example, although certain exemplary embodiments have been described above with reference to a unitary coupling 18, it is contemplated that coupling 18 can also include multiple constituent parts that are mated together during assembly of catheter 10.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An atraumatic coupling and sensor combination for securing a first shaft segment to a second shaft segment, wherein the first shaft segment and the second shaft segment have differing outer diameters, the atraumatic coupling and sensor combination comprising:
    a sensor having a hollow core; and
    a coupling comprising:
        a proximal portion having an exterior surface, the exterior surface of the proximal portion including a plurality of ribs, and wherein an outer diameter of the proximal portion is not greater than an inner diameter of the first shaft segment; and
        a distal portion, the distal portion having an exterior surface that tapers from a point at which the proximal portion meets the distal portion to a distal tip of the distal portion, and wherein and outer diameter of the distal portion at the point at which the proximal portion meets the distal portion is about equal to an outer diameter of the first shaft segment,
        wherein at least the distal portion defines an interior cavity of the coupling, and
        wherein a diameter of the interior cavity of the coupling is not smaller than an outer diameter of the second shaft segment;
    wherein the proximal portion of the coupling is inserted into the hollow core of the sensor.

2. The coupling according to claim 1, wherein the coupling comprises a clear polymeric material.

3. A method of manufacturing a catheter, comprising:
    providing a proximal shaft having a first diameter, a distal shaft having a second diameter different from the first diameter, a coupling having a hollow interior, and a sensor having a hollow core,
    wherein a proximal portion of the coupling comprises:
        a first sub-portion having an outer diameter small enough to allow insertion into the hollow core of the sensor; and
        a second sub-portion having an outer diameter small enough for insertion into the distal portion of the proximal shaft, but too large for insertion into the hollow core of the sensor, the second sub-portion being positioned distally of the first sub-portion;
    inserting a proximal portion of the distal shaft into the hollow interior of the coupling through a distal end of the coupling;
    inserting the proximal portion of the coupling into the hollow core of the sensor;
    inserting the proximal portion of the coupling and the sensor into the proximal shaft through a distal end of the proximal shaft;
    securing the distal shaft to the coupling; and
    securing the proximal shaft to the coupling.

4. The method according to claim 3, wherein the hollow interior of the coupling includes an inner abutment surface, and wherein inserting a proximal portion of the distal shaft into the hollow interior of the coupling through a distal end of the coupling further comprises advancing the proximal portion of the distal shaft into the hollow interior of the coupling until a proximal end of the distal shaft abuts the inner abutment surface.

5. The method according to claim 3, wherein an exterior surface of the coupling includes an outer abutment surface, and wherein inserting a proximal portion of the coupling into the proximal shaft through a distal end of the proximal shaft further comprises advancing the proximal portion of the coupling into the proximal shaft until the distal end of the proximal shaft abuts the outer abutment surface.

6. The method according to claim 3, wherein at least one of securing the distal shaft to the coupling and securing the proximal shaft to the coupling comprises using an ultraviolet curing adhesive.

* * * * *